United States Patent [19]
Makovec et al.

[11] Patent Number: 5,744,607
[45] Date of Patent: Apr. 28, 1998

[54] BASIC DERIVATIVES OF GLUTAMIC ACID AND ASPARTIC ACID AS GASTRIN OR CHOLECYSTOKININ ANTAGONISTS

[75] Inventors: Francesco Makovec; Lucio C. Rovati; Luigi A. Rovati, all of Monza, Italy

[73] Assignee: Rotta Research Laboratorium S.p.A., Milan, Italy

[21] Appl. No.: 733,568

[22] Filed: Oct. 18, 1996

Related U.S. Application Data

[62] Division of Ser. No. 318,651, Oct. 11, 1994, Pat. No. 5,587,479.

[30] Foreign Application Priority Data

Apr. 9, 1992 [IT] Italy ................ TO92A0325

[51] Int. Cl.$^6$ .............. C07D 221/20; C07D 401/06; C07D 209/54; A61K 31/40
[52] U.S. Cl. ............ 546/146; 540/1; 540/477; 540/478; 540/480; 540/481; 540/546; 540/582; 540/585; 540/597; 540/602; 540/606; 544/3; 544/60; 544/62; 544/63; 544/124; 544/128; 544/131; 544/132; 544/142; 544/152; 544/153; 544/359; 544/360; 544/363; 544/373; 544/376
[58] Field of Search ................ 540/1, 477, 478, 540/546, 582, 585, 480, 481, 597, 602, 606; 544/3, 60, 62, 63, 124, 128, 131, 132, 142, 152, 153, 359, 360, 363, 373, 376, 379; 546/146, 178, 169, 314–316, 323; 548/452, 465; 549/468, 487

[56] References Cited

PUBLICATIONS

Heintges T; Niederau C. [Applicability of CCK receptor antagonists in physiologic and therapeutic studies]. Einsatzmoglichkeiten von CCK–Rezeptorantagonisten fur physiologische und therapeutische Studien. Zeitschrift Fur Gastroenterologie, 30(5), 337–343, May 1992.
Bohme G A; Blanchard J CTI Cholecystokinins and their receptors. Functional aspects. Les cholecystokinines et leurs recepteurs. Aspects fonctionnels. Therapie, 47 (6) 541–8.
Lye W C; Lee K O; Tay H H Multiple endocrine neoplasia type 1–presenting with impotence. Singapore Medical Journal, 31 (3) 277–9, Mar. 1990.
Svet–Moldavsky G J Dependence of gastro–intestinal tumors on gastro–intestinal hormones: pentagastrin stimulates growth of transplanted colon adenocarcinoma in mice. Biomedicine, 33 (8) 259–61, Aug. 1980.

Lamers C B The significance of gastrin in the pathogenesis and therapy of peptic ulcer disease. Drugs, 35 Suppl 3, 10–16, Mar. 1988.
Jones R S; Meyers W CTI Regulation of hepatic biliary secretion. Annual Review of Physiology, 41, 67–82, Jan. 1979.
Besterman H S; Mallinson C N; Modigliani R; Christofides N D; Pera A; Ponti V; Sarson D L; Bloom S R Gut hormones in inflammatory bowel disease. Scandinavian Journal of Gastroenterology 18 (7) 845–52, Jul. 1983.
Tiseo P J; Yaksh T L The spinal pharmacology of urinary function: studies on urinary continence in the unanaesthetized rat. CIBA Foundation Symposium, 151 91–104; Medline Abstract #91030853, Jan. 1990.
Konturek J W; Konturek S J; Kurek A; Bogdal J; Oleksy J; Rovati L CCK receptor antagonism by loxiglumide and gall bladder contractions in response to cholecystokinin, sham feeding and ordinary feeding in man. GUT, 30 (8) 1136–42, Aug. 1989.

Primary Examiner—Cecilia J. Tsang
Assistant Examiner—Michael Borin
Attorney, Agent, or Firm—Sughrue, Mion, Zinn, Macpeak & Seas, PLLC

[57] ABSTRACT

The invention is directed to glutamic acid and aspartic acid derivatives represented by formula (I):

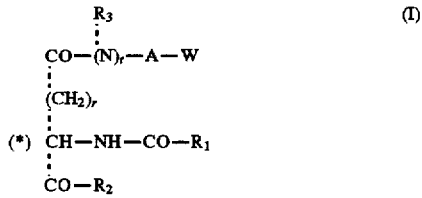

wherein $R_1$ is selected from the group consisting of unsubstituted, mono- or di-substituted phenyl groups, unsubstituted, mono- or di-substituted phenylamino groups, a 2(beta)naphthyl group, and heterocyclic, monocyclic and dicyclic groups; $R_2$ is selected from heterocyclic spiro groups, aminoalkyladamantyl groups, alkylamino groups, $C_4$–$C_{10}$ cycloalkylamino groups and dicyclic amino groups (condensed); $R_3$ is H, $CH_3$ or $C_2H_5$; A is a bond or a linear or branched alkylene group having from 1 to 4 carbon atoms; W is a tertiary amino group or a heterocyclic group; and r is 1 or 2. The compounds have a potent antagonistic effect on gastrin and cholecystokinin and can be used to treat diseases which are linked to imbalances in the physiological levels of gastrin, cholecystokinin or other biologically active polypeptides related thereto.

18 Claims, No Drawings

BASIC DERIVATIVES OF GLUTAMIC ACID AND ASPARTIC ACID AS GASTRIN OR CHOLECYSTOKININ ANTAGONISTS

This is a Divisional of application Ser. No. 08/318,651 filed Oct. 11, 1994, now U.S. Pat. No. 5,587,479.

The subject of the present invention is basic derivatives of glutamic acid and asparatic acid which can be represented by the general formula indicated below:

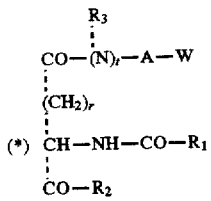 (I)

and in which r is 1 or 2;

$R_1$ is selected independently from:
unsubstituted phenyl; mono- or di-substituted phenyl groups in which the substituents are selected from the halogens (chloro, fluoro, and bromo), linear or branched $C_1$–$C_4$ alkyl groups, and nitro, cyano, methoxy, and trifluoromethyl groups; an unsubstituted phenylamino group; phenylamino groups mono- or di-substituted as described above for the phenyl group; the 2(beta)-naphthyl group; heterocyclic, monocyclic or dicyclic groups selected from an unsubstituted pyridyl group, pyridyl groups mono- or di-substituted with methyl, chloro, furyl (2- or 3-yl), indolyl (2- or 3-yl), isoindolyl (3-yl), benzofuranyl (2- or 3-yl) quinolinyl (2- or 3-yl) or isoquinolinyl (3-yl);

$R_2$ is selected independently from:
1) a heterocyclic spiro group represented by:

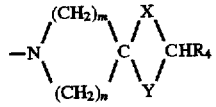

in which m and n are selected independently and may have values of between 1 and 3, provided that the ring formed consists of at least 5 atoms, X and Y are selected independently from (CH—$R_4$)$_z$, TCH$_2$ and CH$_2$T in which T is O or S, and in which $R_4$ is a group selected independently from H, linear and branched $C_1$–$C_4$ alkyl groups, OCH$_3$, and OH, and z may have values of from 0 to 3, provided that the ring formed consists of at least 3 atoms;

2) an aminoalkyladamantyl group represented by:

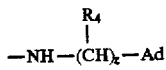

in which z and $R_4$ have the meanings given above and Ad is adamantyl (1- or 2-yl);

3) an alkylamino group represented by:

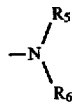

in which $R_5$ is a linear or branched alkyl chain containing from 4 to 10 carbon atoms or a $C_5$–$C_{10}$ cycloaklyl group, or a linear or branched alkoxyalkyl group containing from 4 to 7 carbon atoms, and $R_6$ is selected independently from H, alkyl groups, linear and branched alkoxyalkyl groups containing from 4 to 7 carbon atoms, and $C_5$–$C_{10}$ cycloalkyl groups;

4) a $C_4$–$C_{10}$ cycloalkylamine;
5) a dicyclic amino group (condensed) represented by:

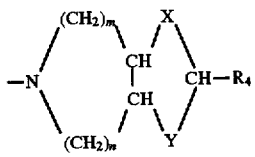

and in which m, n, X, Y, and $R_4$ have the meanings given above;

$R_3$ is H, CH$_3$ or C$_2$H$_5$;

A is a bond or a linear or branched alkylene group comprising from 1 to 4 carbon atoms;

W may be:
1) a tertiary amino group represented by:

in which $R_7$ and $R_8$ are, independently hydrogen or a linear or branched alkyl group comprising from 1 to 5 carbon atoms, provided that $R_7$ and $R_8$ are not both hydrogen;

2) a heterocyclic group represented by:

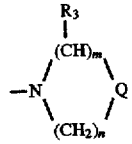

in which $R_3$, m and n have the meanings given above and Q may be a bond, CH$_2$, oxygen, sulphur or nitrogen, N-substituted with $R_9$, $R_9$ being a group selected independently from H, linear and branched $C_1$–$C_4$ alkyl groups, phenyl and benzyl groups, of which the aromatic groups may be unsubstituted or mono- or di-substituted as described for the phenyl group in $R_1$;

3) a heterocyclic group represented by:

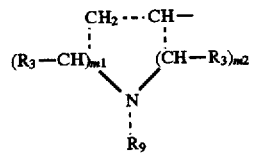

in which m1 and m2 are selected independently and may have values of between 0 and 3 and $R_3$ and $R_9$ have the meanings given above;

4) a heterocyclic group represented by:

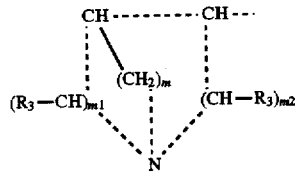

in which m, m1, m2 and $R_3$ have the meanings given above; t is always 1; it may also have a value of 0, but only if W is a heterocyclic group selected from group 2, in which Q is N—$R_9$.

The stereochemistry of the compounds claimed at the chiral centre marked with an asterisk in formula (I) may be racemic (R, S), R (rectus), or S (sinister), r is preferably 2, and R₃ is preferably hydrogen.

According to the nature of the substitutents at $R_1$, $R_2$, A and W, the compounds of the present invention have been shown to have a potent antagonistic effect on gastrin (anti-CCK-B activity) and on cholecystokinin (anti-CCK-A activity) and can thus be used to advantage in the treatment of various diseases in man which are linked to imbalances in the physiological levels of gastrin, CCK, or other biologically active polypeptides related thereto, both at the level of the gastro-intestinal system and at the level of the central nervous system (CNS), or in other organs or systems in which these biologically active peptides play a physiological or pathological role. For example, it is possible to predict the advantageous use of these compounds, at the gastro-intestinal level, for the treatment of diseases linked to disturbances of motility and mucotrophism such as colitis, biliary dyskinesia, pancreatitis, gastritis, peptic ulcers and certain forms of intestinal tumours which are sustained by gastrin or polypeptide hormones related thereto, and at the level of the CNS, for the treatment of mental disorders such as, for example, anorexia, psychosis and anxiety states. Another use could be the treatment and prevention of some eye conditions such as, for example, myosis brought about in the course of the surgical treatment of cataracts or of chronic eye inflammation. As well as being active at the receptor level, many of the compounds of the invention also have an intrinsic antispastic effect on muscles, acting directly at the level of the smooth muscle cells. Thus, some of the compounds of the invention have very potent myorelaxant activity even on areas, such as the urino-genital area, which are not connected with the neurophysiological mediators mentioned above, that is, gastrin and CCK, but, inter alia, also linked to a potent anti-serotoninic action. As a result of this potent myorelaxant effect, it is also possible to predict their favourable use for the treatment of pathological conditions such as, for example, incontinence, other problems with urination or, more generally, spasms and dyskinesia of the ureteral, vesical and uterine musculature.

The method of preparing the derivatives of the invention consists of the amidation of acid derivatives of formula (II):

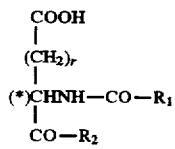

in which r, $R_1$ and $R_2$ have the meanings given above, with suitable amines of formula (III):

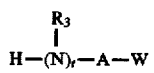

in which $R_3$, t, A and W have the meanings given above, to give the corresponding derivatives of formula (I) according to the following scheme:

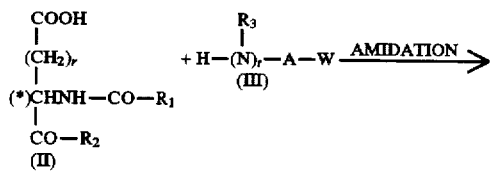

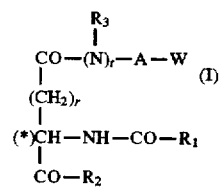

where (*) indicates the chiral centre of the molecule.

The amidation process is preferably effected with the use of the mixed anhydride method, in an inert solvent, at a temperature of between −15° and +15° or by other suitable conventional methods.

The compounds of formula (I) may be isolated from the reaction mass as such, or in the form of salts by reacting them, in an inert solvent, with the appropriate quantities of inorganic acids such as, for example, hydrochloric acid, or organic acids such as, for example, oxalic acid or maleic acid.

The starting acid derivatives of formula (II) were prepared as described (Makovec et al, J. Med. Chem. 35 (1992), 28–38) and the amines of formula (III) are available commercially or were prepared by conventional methods described in the literature. The following example is given in order further to illustrate the invention:

EXAMPLE 1

Preparation of: (RS) 1-[4'-(ethylenamino)morpholinyl]-1-oxo-4-[(3,4-dimethylbenzoyl)-amino]-5-(dipentylamino)-5-oxopentane, (compound 44).

60 g (0.1433 moles) of (R, S) 4-[(3,4-dimethylbenzoyl)amino]-5-(dipentylamino)-5-oxopentanoic acid [tomoglumide, CAS Registry Number: 102742-69-8] and 20 ml of triethylamine (0.1435 moles) were dissolved in 600 ml of tetrahydrofuran and the mixture was cooled to −10° C. This temperature was maintained and 14 ml of ethyl chloroformate (0.1469 moles) were added. Upon completion of the addition, the mixture was left to react for 15 minutes, still at low temperature and then 20 ml of 4-(2-aminoethyl)morpholine (0.1535 moles) were added slowly and the temperature was kept below −5° C. Upon completion of the addition, the reaction mass was kept at low temperature for a further hour and then at ambient temperature for about 12 hours. The solvent was evaporated; the solid obtained was taken up with water and filtered. It was dried in an oven to give 57 g (0.1074 moles) of the product with a yield of 75%.

50 g (0.0942 moles) of the free base obtained was suspended in 250 ml of ethyl acetate and at 5° a solution of HCl in acetone (10% excess) was quickly added dropwise. The product started to precipitate almost immediately and was filtered and washed with ethyl acetate and isopropyl ether. It was dried in air bath at −60° C. to give 49 g of the crude product which was crystallised with ethyl acetate. After cooling, the precipitate was filtered and dried in an air bath at 60° C. to give 46 g (0.0811 moles) of the product with an overall yield of 70.5%.

M.P. 150°–53° C.

TLC (nBuOH/AcOH/H₂O 5:2:2) pure, rf 0.65.

All the compounds of formula (I) were synthesised with the use of the same method (see the scheme given above) Table 1 below gives some of the compounds obtained with some of their identifying characteristics.

TABLE 1

DERIVATIVES OF FORMULA

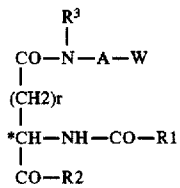

| COMPOUND (*Note 1) | R1 | R2 | R3<br>\|<br>—N—A | W |
|---|---|---|---|---|
| 1 | 3,5-dichloro-phenyl | 8-azaspiro[4.5]decan-8-yl | — | 4-methyl-1-piperazinyl |
| 2 | 3,5-dichloro-phenyl | 8-azaspiro[4.5]decan-8-yl | — | 4-methyl-1-piperazinyl |
| 3 | 3,5-dichloro-phenyl | 8-azaspiro[4.5]decan-8-yl | ethylenamino | 4-morpholinyl |
| 4 | 3,5-dichloro-phenyl | 8-azaspiro[4.5]decan-8-yl | ethylenamino | dimethylamino |
| 5 | 3,5-dichloro-phenyl | 8-azaspiro[4.5]decan-8-yl | ethylenamino | dimethylamino |
| 6 | 3,5-dichloro-phenyl | 8-azaspiro[4.5]decan-8-yl | ethylenamino | 4-methyl-1-piperazinyl |
| 7 | 3-chloro-phenyl | 8-azaspiro[4.5]decan-8-yl | — | 4-methyl-1-piperazinyl |
| 8 | 2-pyridyl | 8-azaspiro[4.5]decan-8-yl | ethylenamino | 4-morpholinyl |
| 9 | 3-trifluoromethyl-phenyl | 8-azaspiro[4.5]decan-8-yl | ethylenamino | 4-morpholinyl |
| 10 | 2-furyl | 8-azaspiro[4.5]decan-8-yl | ethylenamino | 4-morpholinyl |
| 11 | 3,5-dichloro-phenyl | 8-azaspiro[4.5]decan-8-yl | — | 2-amino-quinuclidyl |
| 12 | 2-naphthyl | 8-azaspiro[4.5]decan-8-yl | — | 4-methyl-1-piperazinyl |
| 13 | 3,5-dichloro-phenyl | 3-azaspiro[5.5]-undecan-3yl | — | 4-methyl-1-piperazinyl |
| 14 | 3,4-dimethyl-phenyl | butylamino | ethylenamino | 4-morpholinyl |
| 15 | 3,4-dimethyl-phenyl | butylamino | propylenamino | 4-benzyl-1-piperazinyl |
| 16 | 3,4-dimethyl-phenyl | pentylamino | ethylenamino | 4-morpholinyl |
| 17 | 4-nitrophenyl | pentylamino | ethylenamino | 4-morpholinyl |
| 18 | 3,4-difluoro-phenyl | pentylamino | ethylenamino | 4-morpholinyl |
| 19 | 3,4-dimethyl-phenyl | pentylamino | ethylenamino | 4-benzyl-1-piperazinyl |
| 20 | 3,4-dimethyl-phenyl | pentylamino | propylenamino | 4-benzyl-1-piperazinyl |
| 21 | 3,4-dimethyl-phenyl | hexylamino | ethylenamino | 4-morpholinyl |
| 22 | 3,4-dimethyl-phenyl | hexylamino | propylenamino | 4-benzyl-1-piperazinyl |
| 23 | 3-chloro-phenyl | (3,3-dimethylbutyl)amino | — | 4-methyl-1-piperazinyl |
| 24 | 3-chloro-phenylamino | (3-ethyl-3-methyl-pentyl)-amino | ethylenamino | 4-morpholinyl |
| 25 | 3,4-dimethyl-phenyl | dibutylamino | ethylenamino | dimethylamino |
| 26 | 3,4-dimethyl-phenyl | dibutylamino | ethylenamino | diethylamino |
| 27 | 3,4-dimethyl-phenyl | dibutylamino | propylenamino | dimethylamino |
| 28 | 3,4-dimethyl-phenyl | dibutylamino | ethylenamino | 4-morpholinyl |
| 29 | 3,4-dimethyl-phenyl | dibutylamino | propylenamino | 4-morpholinyl |
| 30 | 3,4-dimethyl-phenyl | dibutylamino | ethylenamino | 1-piperidinyl |
| 31 | 3,4-dimethyl-phenyl | dibutylamino | methylamino | 1-ethyl-pyrrolidin-2-yl |
| 32 | phenyl | dipentylamino | ethylenamino | 4-morpholinyl |
| 33 | 4-methyl-phenyl | dipentylamino | ethylenamino | 4-morpholinyl |
| 34 | 4-cyano-phenyl | dipentylamino | ethylenamino | 4-morpholinyl |
| 35 | 3,4-dimethoxy-phenyl | dipentylamino | ethylenamino | 4-morpholinyl |
| 36 | 4-isopropyl-phenyl | dipentylamino | ethylenamino | 4-morpholinyl |
| 37 | 3,4-dichloro-phenyl | dipentylamino | ethylenamino | 4-morpholinyl |
| 38 | 3,4-dichloro-phenyl | dipentylamino | propylenamino | 4-morpholinyl |
| 39 | 3,5-dichloro-phenyl | dipentylamino | ethylenamino | 4-morpholinyl |
| 40 | 3,4-dimethyl-phenyl | dipentylamino | ethylenamino | dimethylamino |
| 41 | 3,4-dimethyl-phenyl | dipentylamino | propylenamino | dimethylamino |
| 42 | 3,4-dimethyl-phenyl | dipentylamino | ethylenamino | diethylamino |
| 43 | 3,4-dimethyl-phenyl | dipentylamino | propylenamino | diethylamino |
| 44 | 3,4-dimethyl-phenyl | dipentylamino | ethylenamino | 4-morpholinyl |
| 45 | 3,4-dimethyl-phenyl | dipentylamino | ethylenamino | 4-morpholinyl |
| 46 | 3,4-dimethyl-phenyl | dipentylamino | ethylenamino | 4-morpholinyl |
| 47 | 3,4-dimethyl-phenyl | dipentylamino | propylenamino | 4-morpholinyl |
| 48 | 3,4-dimethyl-phenyl | dipentylamino | ethylenamino | 4-methyl-1-piperazinyl |
| 49 | 3,4-dimethyl-phenyl | dipentylamino | propylenamino | 4-methyl-1-piperazinyl |
| 50 | 3,4-dimethyl-phenyl | dipentylamino | ethylenamino | 4-benzyl-1-piperazinyl |
| 51 | 3,4-dimethyl-phenyl | dipentylamino | propylenamino | 4-benzyl-1-piperazinyl |
| 52 | 3,4-dimethyl-phenyl | dipentylamino | — | 4-methyl-1-piperazinyl |
| 53 | 3,4-dimethyl-phenyl | dipentylamino | ethylenamino | 1-pyrrolidinyl |
| 54 | 3,4-dimethyl-phenyl | dipentylamino | propylenamino | 1-piperidinyl |
| 55 | 3,4-dimethyl-phenyl | dipentylamino | ethylenamino | 1-piperidinyl |
| 56 | 3,4-dimethyl-phenyl | dipentylamino | amino | 4-methyl-1-piperazinyl |
| 57 | 3,4-dimethyl-phenyl | dipentylamino | methylamino | 1-methyl-4-piperidinyl |
| 58 | 3,4-dimethyl-phenyl | dipentylamino | methylenamino | 1-ethyl-pyrrolidin-2-yl |
| 59 | 3-quinolinyl | dipentylamino | ethylenamino | 4-morpholinyl |
| 60 | 3,4-dichloro-phenyl | dipentylamino | — | 4-methyl-1-piperazinyl |

TABLE 1-continued

| | | | | |
|---|---|---|---|---|
| 61 | 2-naphthyl | dipentylamino | ethylenamino | 4-morpholinyl |
| 62 | 3-chloro-phenyl | [2-(1-adamantyl)ethyl]amino | ethylenamino | 4-morpholinyl |
| 63 | 3-chloro-phenylamino | [2-(1-adamantyl)ethyl]amino | ethylenamino | 4-morpholinyl |
| 64 | 3,4-dimethyl-phenyl | (3-methoxypropyl)-pentylamino | ethylenamino | 4-morpholinyl |
| 65 | 3-chloro-phenyl | decahydroisoquinolin-2-yl | ethylenamino | 4-morpholinyl |
| 66 | 3-chloro-phenyl | cyclooctylamino | ethylenamino | 4-morpholinyl |
| 67 | 3-chloro-phenyl | octamethylenimino | ethylenamino | 4-morpholinyl |
| 68* | 3-chloro-phenyl | (3-ethyl-3methyl-pentyl)-amino | ethylenamino | 4-morpholinyl |
| 69* | 3,4-dichloro-phenyl | dipentylamino | ethylenamino | 4-morpholinyl |
| 70* | 3,5-dichloro-phenyl | 8-azaspiro[4.5]decan8-yl | — | 4-methyl-1-piperazinyl |

| COMPOUND (*Note 1) | FORMULA | MELTING POINT (C)° | TLC (Rf) (*Note 2) | SPECIFIC ROTATION (Configuration) (*Note 3,4) | |
|---|---|---|---|---|---|
| 1 | C26H36Cl2N4O3 × HCl | 119/22 | 0.56 | −66.4 | (R) |
| 2 | C26H36Cl2N4O3 × HCl | 115/19 | 0.53 | +66.5 | (S) |
| 3 | C27H38Cl2N4O4 | 69/72 | 0.60 | −36.99 | (R) |
| 4 | C25H36Cl2N4O3 × C2H2O4 | 85/91 | 0.61 | −18.4* | (R) |
| 5 | C27H40Cl2N4O3 × HCl | 109/114 | 0.64 | −52.2 | (R) |
| 6 | C28H41Cl2N5O3 × C8H8O8 | 165/66 | 0.56 | −11.9* | (R) |
| 7 | C26H37ClN4O3 × HCl | 113/116 | 0.54 | −69.1 | (R) |
| 8 | C26H39N5O4 × 2HCl | 69/71 (dec) | 0.53 | −57.4 | (R) |
| 9 | C28H39F3N3O4 | 87/90 | 0.57 | −52.4 | (R) |
| 10 | C25H38N4O5 | 101/103 | 0.58 | −70.8 | (R) |
| 11 | C28H38Cl2N4O3 × HCl | 155/61 | 0.53 | −39.5 | (R) |
| 12 | C30H40N4O3 × HCl | 110/113 | 0.58 | −84.7 | (R) |
| 13 | C27H38Cl2N4O3 × HCl | 121/26 | 0.66 | −69.6 | (R) |
| 14 | C24H38N4O4 | 127/30 | 0.51 | 0 | (R,S) |
| 15 | C32H47N5O3 × 2 HCl | 161/65 | 0.54 | 0 | (R,S) |
| 16 | C25H40N4O4 | 118/20 | 0.55 | 0 | (R,S) |
| 17 | C23H35N5O6 | 138/41 | 0.60 | 0 | (R,S) |
| 18 | C23H34F2N4O4 | 135/38 | 0.52 | 0 | (R,S) |
| 19 | C32H47N5O3 | 134/37 | 0.53 | 0 | (R,S) |
| 20 | C33H49N5O3 × 2 HCl | 100/07 | 0.57 | 0 | (R,S) |
| 21 | C26H42N4O4 | 140/42 | 0.62 | 0 | (R,S) |
| 22 | C34H51N5O3 × 2 HCl | 140/44 | 0.60 | 0 | (R,S) |
| 23 | C23H35ClN4O3 × HCl | 113/15 | 0.58 | −37.3 | (R) |
| 24 | C26H42ClN5O4 | 165/67 | 0.59 | +24.9 | (R) |
| 25 | C26H44N4O3 | 110/11 | 0.51 | 0 | (R,S) |
| 26 | C28H48N4O3 | 104/07 | 0.58 | 0 | (R,S) |
| 27 | C27H46N4O3 | 96/9 | 0.53 | 0 | (R,S) |
| 28 | C28H46N4O4 | 138/40 | 0.57 | 0 | (R,S) |
| 29 | C29H48N4O4 | 61/63 | 0.56 | 0 | (R,S) |
| 30 | C29H48N4O3 | 109/11 | 0.63 | 0 | (R,S) |
| 31 | C29H48N4O3 | 73/76 | 0.51 | 0 | (R,S) |
| 32 | C28H46N4O4 | 109/11 | 0.55 | 0 | (R,S) |
| 33 | C29H48N4O4 | 109/12 | 0.60 | 0 | (R,S) |
| 34 | C29H45N5O4 | 99/100 | 0.65 | 0 | (R,S) |
| 35 | C30H50N4O6 | 129/39 | 0.63 | 0 | (R,S) |
| 36 | C31H52N4O4 | 110/12 | 0.65 | 0 | (R,S) |
| 37 | C28H44Cl2N4O4 | 116/19 | 0.65 | 0 | (R,S) |
| 38 | C29H46Cl2N4O4 | 88/91 | 0.66 | 0 | (R,S) |
| 39 | C28H44Cl2N4O4 | 129/31 | 0.67 | 0 | (R,S) |
| 40 | C28H48N4O3 | 105/07 | 0.55 | 0 | (R,S) |
| 41 | C29H50N4O3 | 70/72 | 0.60 | 0 | (R,S) |
| 42 | C30H52N4O3 | 85/88 | 0.59 | 0 | (R,S) |
| 43 | C31H54N4O3 | 64/65 | 0.60 | 0 | (R,S) |
| 44 | C30H50N4O4 × HCl | 150/53 | 0.65 | 0 | (R,S) |
| 45 | C30H50N4O4 | 120/22 | 0.66 | +12.4* | (R) |
| 46 | C30H50N4O4 | 118/20 | 0.66 | −12.0* | (S) |
| 47 | C31H52N4O4 | 80/83 | 0.63 | 0 | (R,S) |
| 48 | C31H53N5O3 | 98/100 | 0.50 | 0 | (R,S) |
| 49 | C32H55N5O3 | 84/85 | 0.55 | 0 | (R,S) |
| 50 | C37H57N5O3 × 2HCl | 185/89 | 0.62 | 0 | (R,S) |
| 51 | C38H59N5O3 × 2HCl | 138/41 | 0.52 | 0 | (R,S) |
| 52 | C29H48N4O3 | 81/83 | 0.59 | 0 | (R,S) |
| 53 | C30H50N4O3 | 127/29 | 0.61 | 0 | (R,S) |
| 54 | C32H54N4O3 | 92/94 | 0.56 | 0 | (R,S) |
| 55 | C31H52N4O3 | 101/03 | 0.63 | 0 | (R,S) |
| 56 | C29H49N5O3 | 118/20 | 0.59 | 0 | (R,S) |
| 57 | C31H52N4O3 × HCl | 173/76 dec | 0.61 | 0 | (R,S) |
| 58 | C31H52N4O3 | 77/80 | 0.65 | 0 | (R,S) |
| 59 | C31H47N5O4 | 114/15 | 0.49 | −16.3 | (R) |

TABLE 1-continued

| | | | | | |
|---|---|---|---|---|---|
| 60 | C27H42Cl2N4O3 × HCl | 81/83 | 0.64 | −41.3 | (R) |
| 61 | C32H48N4O4 | 126/27 | 0.54 | −8.4 | (R) |
| 62 | C30H43ClN4O4 | 187/89 | 0.58 | +11.5 | (R) |
| 63 | C30H44ClN5O4 | 196(dec) | 0.59 | +22.3 | (R) |
| 64 | C29H48N4O5 | 111/12 | 0.67 | 0 | (R,S) |
| 65 | C27H39ClN4O4 × HCl | 116/18 | 0.51 | −62.0 | (R) |
| 66 | C26H39ClN4O4 | 152/54 | 0.57 | 0 | (R,S) |
| 67 | C26H39ClN4O4 × HCl | 54/47 | 0.49 | 0 | (R,S) |
| 68* | C25H39ClN4O4 | 142/44 | 0.62 | 0 | (R,S) |
| 69* | C27H42Cl2N4O4 | 135/36 | 0.65 | +12.4 | (R) |
| 70* | C25H34Cl2N4O3 × HCl | 263/66 | 0.50 | +2.6 | (R) |

Note:
1) The compounds 1–67 belong to the glutamic series (r = 2)
The compounds 68–70 belong to the aspartic series (r = 1)
2) The thin-layer chromatography (TLC) was carried out with the use of thin sheets of silica gel and with BuOH-Acetic acid - H$_2$(5/2/2:v/v) as the eluent.
3) The determination of the specific rotatory power was carried out in chloroform, except for the compounds 4, 6, 45 and 46, for which methanol was used, with the use of sodium as a yellow light source (D).
4) R and S denote the Rectus (R) and Sinister (S) configurations.

Description of Pharmacological Activity

1) Activity against gastric secretion in the rat

The investigation of the activity against gastric secretion performed by the compounds of the invention by means of an antigastrin mechanism was carried out in vivo in anaesthetized rats with the use of male animals weighing about 200g. Gastric secretion was stimulated with pentagastrin and the method of K. S. Lai [Gut 5, (1964)., 327–341] was used, slightly modified.

After tracheotomy, the oesophagus and duodenum were cannulated. Perfusion was carried out with a tepid solution (37° C.) of 0.25 mM NaOH which was passed through the stomach by means of a peristaltic pump at a constant flow rate of 1 ml/minute. After stabilization for 20 minutes, the stimulant, dissolved in a physiological solution, was perfused for 120 minutes at a dose of 30 mcg/kg/h in a volume of 0.95 ml/hour. After perfusion for 60 minutes (the basal simulation), the product under test was administered intravenously (I.V.) as a bolus and the perfusion of the stimulant was continued for a further 60 minutes. The acid secretion was recorded continuously as a function of time.

The activity of the product was evaluated as the percentage reduction in the secreted acidity after the administration of the product compared with the basal acidity measured during the first 60 minutes of collection in the presence of pentagastrin alone.

The antagonistic compounds tested were administered in different doses in order to be able to calculate an ID50, that is, the dose (in mg/kg I.V.) which can he effect of the pentagastrin by 50%.

The results obtained are shown in the table below (Tab. 2) in which the activities of the compounds are expressed as ID50s under the stimulus of 30 mcg/kg/h of pentagastrin.

TABLE 2

Antagonistic activity (ID50 mg/kg I.V.) towards acid secretion induced by pentagastrin (30 mcg/kg/h) in the rat.

| Compounds | Activity (ID50) | Compounds | Activity (ID50) |
|---|---|---|---|
| 1 | 9.0 | 44 | IN (30) |
| 2 | 24.8 | 68 | 31.0 |
| 3 | 12.8 | 70 | 18.9 |
| 4 | IN(*) (30) | CR 2194 | 11.0 |

TABLE 2-continued

Antagonistic activity (ID50 mg/kg I.V.) towards acid secretion induced by pentagastrin (30 mcg/kg/h) in the rat.

| Compounds | Activity (ID50) | Compounds | Activity (ID50) |
|---|---|---|---|
| 6 | IN (20) | proglumide | 500 |
| 13 | 8.5 | lorglumide | IN (100) |
| 23 | 25.0 | | |

Note:
(*)IN (inactive), when the antisecretive activity at the dose given is less than 20%.

It can be seen from an examination of this table that many of the basic compounds of the invention have potent antigastrin activity.

The antigastrin activity is particularly favourable in the case of the derivatives of glutamic acid (r=2) when $R_1$ is 3,5-dichloro-phenyl, when the amino group $R_2$ is the azaspiro[4.5]decan-8-yl group or the azaspiro[5.5]-undecan-3-yl group, A is a bond, and W is the 4-methyl-1-piperazinyl group (compounds 1 and 13). It can be seen that, in this experimental model, the most potent of the compounds of the invention are about 50 times more active than the reference antigastrin compound, proglumide. It is also interesting to note that the CCK-A antagonist, lorglumide, is completely inactive up to a dose of 100 mg/kg. The antigastrin activities of these compounds are stereospecific as can be seen by comparing the activity of the compound 1, derived from the R (rectus) series, which is about three times higher than that of its S (sinister) enantiomer, that is, the compound 2. The compound 1 is about 1.2 times more active than CR 2194, its acid "parent compound", and this ratio becomes about 1.5 when calculated on a molar basis. This shows that, contrary to what was known up to now, the gastrin (CCK-B) receptor is also sensitive to basic competitors.

2) Anticholecystokinin (anti-CCK-A) activity in vitro

In order to check the hypothesis that the molecular conformations of the compounds of the invention are such that, as well as their antagonistic activity towards gastrin (CCK-B), they also have antagonistic activity towards CCK-A, that is, the peripheral CCK which is active particularly at the level of the pancreas and the smooth musculature of the gall bladder, the pilorus and the intestine, the ability of some compounds of the invention and of some corresponding acid starting derivatives to inhibit the binding of [125-I]-[Bolton-Hunter]-CCK-8 to the cholecystokinin receptors of the pancreatic cells of the rat was tested, in comparison with the displacement induced by cold (unmarked) CCK-8.

The pancreatic cells of the rat were prepared as described by Makovec et al. (reference cited) so as to produce about $5 \times 10^6$ cells/ml. The cells were then incubated together with the radioactive tracer and the compounds under test for 30 minutes at 37° C.

After the supernatant liquid had been discarded, the radioactivity associated with the pellet was determined with a gamma counter (80% efficiency). The specific binding was determined as the difference between the binding in the absence and in the presence of $10^{-6}$M CCK-8 (70% on average).

The results obtained are given in Table 3, in which the IC50, that is the concentration (in moles/liter) of the antagonist which can displace 50% of the [125-I]-CCK-8 from the receptor is given.

TABLE 3

Inhibition of the binding of (125-I) (B-H)-CCK-8 to the pancreatic cells of the rat.

| Compounds | IC50 (moles/liter) |
| --- | --- |
| CCK-8 | $0.5 \cdot 10^{-9}$ |
| Compound 1 | $6.6 \cdot 10^{-6}$ |
| Compound 59 | $1.2 \cdot 10^{-6}$ |
| Compound 61 | $2.8 \cdot 10^{-6}$ |
| R-lorglumide | $0.05 \cdot 10^{-6}$ |
| CR 2194 | $13.5 \cdot 10^{-6}$ |

It can be seen from the data given in the table that some of the compounds claimed have a discrete anti-CCK A activity, antagonising the binding of CCK by 50% at concentrations of about $10^6$M, that is about 1000 times greater than those of the specific antagonist CCK-8.

Although it has a possible therapeutic significance, this activity is decidedly less than that of the most potent CCK-A antagonists of the acid series such as, for example, R-lorglumide which seems to be about 25 times more active than the compound 59. The introduction of an amino-amide group in position 1 of 4-benzamido-pentanoic acid for the gastrin antagonists (or CCK-B antagonists), on the other hand, slightly increases their CCK-A-antagonistic activity as can be seen by examining the activity of the compound 1 which is about twice as active as its acidic "parent compound" CR 2194.

3) Anticholecystokinin (anti CCK-B) activity in vitro

Since the radioligand [I-125] [B-H]-CCK-8 does not discriminate between the CCK-A and CCK-B receptors present in the brain, in order better to evaluate the abilities of the compounds of the invention to interact with the central CCK-B receptors, a new ligand, non-sulphated [3-H] [N-methyl-N-leucine]CCK-8 was used which had been found (Knapp et al.; J. Pharmacol. and Exp. Therap. 255 (3) (1990), 1278–1286) to be a very selective ligand for the CCK-B receptors, its affinity for the receptors of the cortex (CCK-B) being about 4000 times greater than for those of the pancreas (CCK-A) in the guinea-pig.

Cerebral cortices of white male guinea pigs were therefore used, according to the method mentioned above, so as to obtain a membrane content/ml corresponding to about 300 mcg of proteins/ml. The membranes were incubated together with the radioactive tracer and the compounds under test for 150 minutes at 25° C. After the supernatant liquid had been discarded, the radioactivity associated with the pellet was determined with a liquid scintillator. The specific binding was determined as the difference between the binding in the absence and in the presence of $5.10^{-6}$M CCK-8. The results obtained are given in Table 4 which gives the IC50, that is, the concentration (in moles/liter) of the antagonist which can displace 50% of the (3-H)[N-methyl-N-leucine]CCK-8 from the receptor.

TABLE 4

Inhibition of binding of (3-H) [N-methyl-N-leucine] CCK-8 to the guinea pig cortical membrane.

| Compounds | IC50 (moles/liter) | Compounds | IC50 (moles/liter) |
| --- | --- | --- | --- |
| 1 | $0.7 \cdot 10^{-6}$ | 23 | IN |
| 2 | IN* | 36 | $81.3 \cdot 10^{-6}$ |
| 3 | $2.8 \cdot 10^{-6}$ | 44 | $65.4 \cdot 10^{-6}$ |
| 4 | $12.5 \cdot 10^{-6}$ | 55 | IN |
| 5 | $2.6 \cdot 10^{-6}$ | 60 | $50.0 \cdot 10^{-6}$ |
| 6 | $3.3 \cdot 10^{-6}$ | 61 | $2.9 \cdot 10^{-6}$ |
| 7 | $6.5 \cdot 10^{-6}$ | R-lorglumide | $9.2 \cdot 10^{-6}$ |
| 11 | $3.8 \cdot 10^{-6}$ | CR 2194 | $2.4 \cdot 10^{-6}$ |
| 13 | $0.6 \cdot 10^{-6}$ | pentagastrin | $3.0 \cdot 10^{-9}$ |

Note
*IN (inactive) when the IC50 is $< 10^{-4}$ M.

It can be seen from the data given in Table 4 that some of the compounds of the invention, such as, for example, the compounds 1 and 13, are potent inhibitors of the binding of [N-methyl-N-leucine]CCK-8 to the receptors of the cortical membranes of guinea-pigs. In fact they are about 3 times more potent than the gastrin antagonist CR 2194 and about 10 times more potent than the CCK-A antagonist R-lorglumide, whereas they are about 200 times less active than the specific antagonist, pentagastrin. It can also be seen that the displacing activity is greatly affected by the stereochemistry of the molecule of the invention. In fact the S enantiomer of the compound 1 (compound 2) is practically inactive in this test, having an IC50 of more than $10^{-6}$M.

4) Anxiolytic activity in the mouse

In order to confirm the hypothesis that the potent activity of some of the compounds of the invention against central CCK-B may be correlated with a possible anxiolytic activity, this potential activity was evaluated in the mouse with the use of the "Black and White Box test". This experimental model, which was carried out according to Costall et al. [Pharm. Biochem. Behav. 32 (1989), 777–785] used a box with dimensions of 45×21×21 (h) cm. divided into two compartments which communicated with each other by means of a 13×5 cm hole. The smaller compartment (⅓ of the total area) had black walls, whereas the larger had transparent walls and was illuminated by a lamp which was placed 20 cm above the box and supplied light at 20 W. Under the floor was an activity meter which registered the movements performed by the animal in the individual compartments. The experiment was started by placing the animal in the centre of the illuminated box; as well at its movements, the time which the animal spent in the dark and in the light and the number of times it moved between the 2 compartments were recorded for five minutes. In general, a control animal tended preferably to stay in the dark compartment where it felt better protected from an unusual enviromental situation which put it in a state of anxiety. In this experimental model (see the reference cited above), a compound having anxiolytic activity decreased the % of movements into the dark in comparison with the total movements, increased the movements between the two light-dark compartments, and increased the % of the total time time spent in the light. The results are given in Table 5 below in which the activities obtained with the compound 1 (the rectus series) and its enantiomer 2 (sinister) tested in comparison with diazepam and the CCK-B antagonist L365-260.

TABLE 5

ANXIOLYTIC ACTIVITY IN THE MOUSE IN THE "BLACK AND WHITE BOX TEST"

| | DOSE mg/kg IP | No. ani-mals | TOTAL MOV. | MOV. DARK (%) TOTAL MOV. | % EFF. VS CONTROL |
|---|---|---|---|---|---|
| CONTROL | — | 15 | 483 | 50 | — |
| COMPOUND 1 | 0.01 | 15 | 478 | 50 | 0 |
| COMPOUND 1 | 0.1 | 15 | 461 | 47 | −5 |
| COMPOUND 1 | 1 | 15 | 471 | 45 | −9 |
| CONTROL | — | 10 | 473 | 52 | — |
| COMPOUND 2 | 0.1 | 10 | 477 | 50 | −4 |
| COMPOUND 2 | 1.0 | 10 | 462 | 50 | −4 |
| CONTROL * | — | 10 | 439 | 50 | — |
| L-365-260 | 0.01. | 10 | 417 | 57 | 12 |
| " | 0.1 | 10 | 446 | 54 | 18 |
| CONTROL * | — | 15 | 459 | 56 | — |
| DIAZEPAM | 1 | 15 | 508# | 53 | −5 |
| DIAZEPAM | 3 | 15 | 539# | 52 | −7 |

| | LIGHT-DARK MOVEMENTS | % EFF. VS CON-TROL | LIGHT TIME (%) TOTAL TIME | % EFF. VS CON-TROL |
|---|---|---|---|---|
| CONTROL | 12.8 | — | 27.7 | — |
| COMPOUND 1 | 13..2 | 3 | 32.3# | 17 |
| COMPOUND 1 | 15.0# | 17 | 35.4# | 28 |
| COMPOUND 1 | 12.9 | 0 | 30.5 | 10 |
| CONTROL | 13.3 | — | 28.2 | — |
| COMPOUND 2 | 13.2 | 0 | 28.3 | 0 |
| COMPOUND 2 | 12.8 | 0 | 27.5 | 0 |
| CONTROL * | 16.2 | — | 27.0 | — |
| L-365-260 | 14.2 | −12 | 27.0 | 0 |
| " | 13.3 | −18 | 31.8 | 18 |
| CONTROL * | 14.5 | — | 24.6 | — |
| DIAZEPAM | 19.9 | +37.2 | 29.3 | 19 |
| DIAZEPAM | 22.3 | +53.8# | 33.6 | 36.7 |

Note: The control group * did not consist of a physiological solution, but of a suspension of methyl cellulose (0.5%) in a 5% (v/v) solution of dimethylsulphoxide-C which was used to dissolve the compounds under test. #A significant difference in comparison with the controls (P < 0.01).

It can be seen from Table 5 that the compound 1 is active for all the parameters tested. Thus, it has anxiolytic activity which results in a reduction in the percentage of movements into the dark in comparison with the total movements, an increase in the number of light-dark movements, and an increase in the time spent in the light, in comparison with the control group. The dose at which the compound is most active is 0.1 mg/kg (I.P.). The effect of the compound has a bell-shaped curve which result is not rare for compounds which are active on the central nervous system. Its S enantiomer (compound 2) was completely inactive in this model, confirming the results obtained in vitro on the binding of the guinea-pig cortex. The potent benzodiazepine-type CCK-B antagonist L-365-260 (Pakard et al TIPS 11 (1990), 271–273) was also active at a dose of 0.1 mg/kg but only for the parameter which relates to the increase in the time spent in the light. The conventional anxiolytic, diazepam, which was tested at doses of 1 and 3 mg/kg was active in a dose-dependent manner for all the parameters tested. Its activity, however, was qualitatively different since this compound also significantly increased the total movements whereas neither of the putative CCK-B antagonists, that is, the compound 1 and the compound L-365-260, seemed to affect this parameter.

5) Antispastic activity in vitro: guinea-pig ureters.

Another interesting aspect of the activity of these products is the potent spasmolytic activity which some of them have on the smooth musculature of mammals. Their activity in the ureters of guinea pigs is given below by way of example. The method of Mitolo-Chieppa et al (Pharm. Res. Comm: 14, 807–814/1992) was used, slightly modified. The guinea-pig ureter, cleaned of fat and of renal tissue, was placed in a bath for isolated organs in the presence of Krebs at a temperature of 37° C. and oxygenated continuously with an oxygen-$CO_2$ mixture (95-5 v/v). The isotonic contractions were detected by means of a force transducer and recorded. After a re-equilibration period of about 45 minutes, the prepared specimen showed a spontaneous rhythmic contractility. A given concentration of the product under test was then introduced into the bath and left in contact with the prepared specimen for five minutes, after which the ureter was washed until its own spontaneous activity was re-established. The myorelaxant activities of the compounds were determined with the use of various concentrations thus determining the IC50 values, that is, the concentration in mcg/l of the compound which could antagonise the spontaneous activity of the prepared specimen by 50% in terms of both the frequency and the force of the contractions. The results obtained are set out in Table 6 below which gives the compounds tested and the IC50s found, which were calculated by the regression method on a set of at least 3 tests at 3 different concentrations for each compound tested.

TABLE 6

Inhibition (IC50) of the spontaneous motility of guinea-pig ureters in vitro

| Com-pound | IC50 (fre-quency) | IC50 (force) | Compound | IC50 (frequency) | IC50 (force) |
|---|---|---|---|---|---|
| 1 | 29 | 23 | 37 | 7 | 8 |
| 2 | 20 | 25 | 40 | 44 | 27 |
| 3 | 4.3 | 4.5 | 41 | 28 | 20 |
| 4 | 121 | IN | 42 | 22 | 18 |
| 6 | IN | IN | 44 | 4 | 5 |
| 16 | IN | IN | 45 | 6 | 8 |
| 25 | IN | 36 | 46 | 1.5 | 1.6 |
| 27 | IN | 33 | 47 | 15 | 12 |
| 28 | 43 | 18 | 51 | 100 | 100 |
| 29 | 17 | 18 | 55 | 18 | 11 |
| 31 | IN | 23 | 58 | 19 | 14 |
| 32 | 22 | IN | 61 | 100 | 32 |
| 33 | 16 | 18 | 64 | IN | 59 |
| 34 | 12 | 12 | Papaverine | 27 | 23 |
| 35 | 16 | 18 | Flavoxate | IN | 29 |
| 36 | 1.5 | 2 | Verapamil | 2.2 | 3 |

It can be seen from Table 6 that, whereas some of the compounds of the invention are not very effective in this model, others such as, for example, the compounds 3, 36, 44 and 46, are extremely active (IC50 about 1–2 mcg/ml for the most active).

For example, the compound 46 is about 20 times more active than Papaverine and Flavoxate and about twice as active as an extremely potent calcium antagonist such as Verapamil. In general, it can be said that the myolytic activity performed in this model is particularly high when $R_1$ is 3,4 dimethylphenyl or 4-isopropylphenyl, $R_2$ is dipentylamino or 8-azaspiro[4.5]decan-8-yl, A is ethylenamino, and W is 4-morpholinyl. The preferred configuration in this case is S (sinister) as can be deduced by comparing the activities of the compound 46 with those of its R enantiomer, the compound 45.

We claim:
1. A compound represented by the general formula

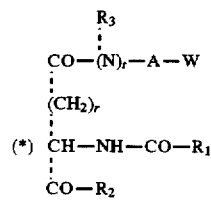

wherein r is 1 or 2;

$R_1$ is independently selected from the group consisting of an unsubstituted phenyl group; a mono- or di-substituted phenyl group in which the substituent is independently selected from the group consisting of a halogen atom, a linear or branched $C_1$-$C_4$ alkyl group, a nitro group, a cyano group, a methoxy group and a trifluoromethyl group; an unsubstituted phenylamino group; a mono- or di-substituted phenylamino group in which the substituent is independently selected from the group consisting of a halogen atom, a linear or branched $C_1$-$C_4$ alkyl group, a nitro group, a cyano group, a methoxy group and a trifluoromethyl group; a 2(beta)naphthyl group; and a heterocyclic, monocyclic or bicyclic group selected from the group consisting of a furyl group (2- or 3-yl), an indolyl group (2- or 3-yl), an isoindolyl group (3-yl), a benzofuranyl group (2- or 3-yl), a quinolinyl group (2- or 3-yl), an isoquinolinyl group (3-yl), an unsubstituted pyridyl group and a mono- or di-substituted group in which the substitutents are methyl or chloro;

$R_2$ is ($a_1$) a $C_4$-$C_{10}$ cycloalkylamino group, or ($b_1$) an alkylamino group represented by:

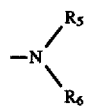

wherein $R_5$ is a linear or branched chain alkyl group having from 4 to 10 carbon atoms, a $C_5$-$C_{10}$ cycloalkyl group, or a linear or branched alkoxyalkyl group having from 4 to 7 carbon atoms; and $R_6$ is selected from the group consisting of a hydrogen atom, an alkyl group, a linear or branched alkoxyalkyl group having from 4 to 7 carbon atoms and a $C_5$-$C_{10}$ cycloalkyl group;

$R_3$ is a hydrogen atom, a $CH_3$ group or a $C_2H_5$ group;

A is a bond or a linear or branched alkylene group having from 1 to 4 carbon atoms;

W is ($a_2$) a tertiary amino group represented by:

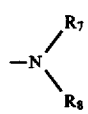

wherein $R_7$ and $R_8$ independently represent a hydrogen atom or a linear or branched alkyl group having from 1 to 5 carbon atoms, provided that $R_7$ and $R_8$ are not both hydrogen atoms;

($b_2$) a heterocyclic group represented by:

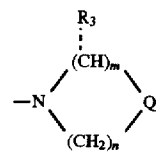

wherein $R_3$ is as defined above, m and n are independently selected integers having values between 1 and 3, provided that the ring formed consists of at least 5 atoms; Q is a bond, a $CH_2$ group, an oxygen atom, a sulphur atom, a nitrogen atom, or N—$R_9$; $R_9$ is a hydrogen atom, a linear or branched $C_1$-$C_4$ alkyl group, a phenyl group or a benzyl group, the aromatic groups of which may be unsubstituted or mono- or di-substituted as described above for the phenyl group in $R_1$;

($c_2$) a heterocyclic group represented by:

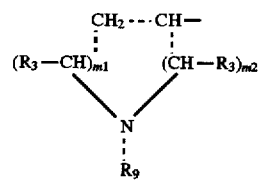

wherein m1 and m2 independently represent a value of between 0 and 3; and $R_3$ and $R_9$ have the above defined meanings;

or ($d_2$) a heterocyclic group represented by:

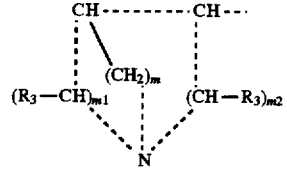

wherein m, m1, m2 and $R_3$ have the above defined meanings;

t is 1, except when Q is N—$R_9$ in ($b_2$), then t is 0 or 1; and pharmaceutically acceptable salts thereof.

2. The compound according to claim 1, wherein $R_1$ is a 3,4-dimethylphenyl group or a 4-isopropylphenyl group; $R_2$ is a dipentylamino group; —$NR_3A$ is an ethylenamino group; W is a 4-morpholinyl group; r is 2; and the stereochemistry of the chiral center is racemic or S.

3. The compound according to claim 1, wherein $R_1$ is a 3,4-dichlorophenyl group, a 2-naphthyl group or a 3-quinolinyl group; $R_2$ is a dipentylamino group; A is a bond or an ethylene group; W is a 4-morpholinyl group or a 4-methyl-1-piperazinyl group, provided that t is zero when W is the 4-methyl-1-piperazinyl group; r is 2; $R_3$ is a hydrogen atom; and the stereochemistry of the chiral center is racemic or R.

4. A pharmaceutical preparation comprising a pharmaceutically effective amount of at least one compound according to claim 1 as an active substance or a pharmaceutically acceptable salt thereof, and a pharmaceutically acceptable carrier.

5. The pharmaceutical preparation according to claim 4, which further comprises a pharmaceutically acceptable inactive ingredient selected from the group consisting of vehicles, binders, flavorings, dispersants, preservatives, humectants and mixtures thereof.

6. A method for antagonizing gastrin activity, comprising administering the pharmaceutical preparation according to claim 4 to a subject in need thereof.

7. A method for antagonizing cholecystokinin activity, comprising administering the pharmaceutical preparation according to claim 4 to a subject in need thereof.

8. A method for treating ulcers, comprising administering the pharmaceutical preparation according to claim 4 to a subject in need thereof.

9. A method for treating intestinal tumors, comprising administering the pharmaceutical preparation according to claim 8 to a subject in need thereof.

10. A method for treating imbalances in the physiological neurone levels of gastrin in the central nervous system, comprising administering the pharmaceutical preparation according to claim 4 to a subject in need thereof.

11. A method for treating biliary dyskinesia, comprising administering the pharmaceutical preparation according to claim 4 to a subject in need thereof.

12. A method for treating colitis, comprising administering the pharmaceutical preparation according to claim 4 to a subject in need thereof.

13. A method for treating pancreatis, comprising administering the pharmaceutical preparation according to claim 4 to a subject in need thereof.

14. A method for treating urinary incontinence, comprising administering the pharmaceutical preparation according to claim 4 to a subject in need thereof.

15. A method for treating neurogenic bladder, comprising administering the pharmaceutical preparation according to claim 4 to a subject in need thereof.

16. A method for treating urinary calculus, comprising administering the pharmaceutical preparation according to claim 4 to a subject in need thereof.

17. A method for treating spastic conditions of the vesico-ureteral and uterine musculature, comprising administering the pharmaceutical preparation according to claim 4 to a subject in need thereof.

18. A method of preparing a derivative of formula (I) in which r, t, $R_1$, $R_2$, $R_3$, A and W have the meanings given in claim 1 and in which the substituents at the chiral centre marked with an asterisk in formula (I) have the (R,S), R or S conformation, consisting of reacting acid derivatives of formula (II):

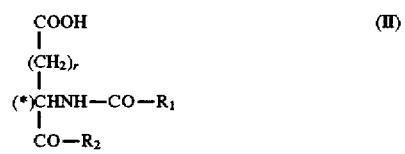

in which r, $R_1$ and $R_2$ have the meanings given above, with suitable amines of formula (III):

in which $R_3$, t, A and W have the meanings given in claim 1, in a molar ratio of from 1 to 3 at a temperature of between −15° C. and +20° C. by the mixed anhydride method or by other equivalent conventional methods of synthesis, and in recovering the basic compounds (I) from the reaction mass either as such or by salification carried out in an inert solvent by suitable pharmaceutically-acceptable organic or inorganic acids.

* * * * *